United States Patent [19]

Davies

[11] Patent Number: 4,642,903

[45] Date of Patent: Feb. 17, 1987

[54] FREEZE-DRIED FOAM DOSAGE FORM

[75] Inventor: J. Desmond Davies, Grosse Pointe Farms, Mich.

[73] Assignee: R. P. Scherer Corporation, Troy, Mich.

[21] Appl. No.: 716,341

[22] Filed: Mar. 26, 1985

[51] Int. Cl.$^4$ ............................................. F26B 5/06
[52] U.S. Cl. ............................................. 34/5; 34/15; 62/1; 62/69; 62/70
[58] Field of Search .................. 34/5, 15, 92; 62/69, 62/70, 1

[56] References Cited

U.S. PATENT DOCUMENTS

| | | | |
|---|---|---|---|
| 3,482,990 | 12/1969 | Pfluger | 34/5 |
| 3,514,518 | 5/1970 | Vadrot | 34/5 |
| 3,579,360 | 5/1971 | Rey | 34/5 |
| 3,653,929 | 4/1972 | Dwyer | 34/5 |
| 3,804,960 | 4/1974 | Barnett | 34/5 |
| 4,178,695 | 12/1979 | Erbeia | 34/5 |
| 4,180,917 | 1/1980 | Neubeck | 34/5 |
| 4,305,502 | 12/1981 | Gregory et al. | 34/5 |

Primary Examiner—Albert J. Makay
Assistant Examiner—David W. Westphal
Attorney, Agent, or Firm—Allegretti, Newitt, Witcoff & McAndrews, Ltd.

[57] ABSTRACT

A method of preparing a freeze-dried foam including an active ingredient, such as a pharmaceutical, nutrient, diagnostic, insecticide or fertilizer, is disclosed.

19 Claims, No Drawings

FREEZE-DRIED FOAM DOSAGE FORM

BACKGROUND OF THE INVENTION

1. Field of the Invention

The present invention relates to methods of preparing products by freeze-drying.

2. Description of the Prior Art

Freeze-drying is a well known method of drying heat-sensitive materials in order to protect them from thermal damage. In the past, preparations containing active ingredients, such as pharmaceuticals, nutrients, diagnostics, fertilizers and insecticides, have been prepared by freeze-drying aqueous solutions or suspensions containing these active ingredients. One problem that has arisen, however, with the use of known freeze-drying processes is cracking of the freeze-dried preparations. Typically, cracking is caused by the stresses set up during ice crystallization. Though cracking is never desirable, it is especially undesirable where drop methods of freezing are employed. In such cases, cracking of the frozen droplets usually results in unusable and inelegant remnants of fractured droplets.

Another problem encountered by use of known freeze-drying methods is a phenonomen called meltback. Meltback occurs when the heat required during the drying process melts the frozen material. As such, meltback defeats the whole purpose of freeze-drying—the removal of water through sublimation as opposed to evaporation. To avoid meltback in conventional freeze-drying methods, only limited amounts of material of limited thickness can be dried at one time. Even with these limitations, conventional freeze-drying methods are not always rapid enough to prevent meltback.

In the area of pharmaceuticals, known freeze-dried dosage forms do not always exhibit fast dissolution rates when brought into contact with appropriate solvents, such as water, saliva or gastrointestinal fluids. Rapid dissolution of pharmaceutical dosage forms can be of critical importance in instances where it is desirable that the pharmaceutial enter the physiological system as soon as possible.

Thus, there is a need for a method of producing freeze-dried preparations that avoid cracking and meltback during the freeze-drying process. In addition, there is a need for freeze-dried pharmaceutical dosage forms that exhibit rapid dissolution upon ingestion.

SUMMARY OF THE INVENTION

It is an object of the present invention to provide a method of freeze-drying an aqueous solution or suspension that prevents or reduces the incidence of cracking of the freeze-dried preparation.

It is an additional object of the present invention to provide a method of freeze-drying wherein the incidence of meltback during the freeze-drying process is reduced or eliminated.

It is a further object of the present invention to provide a method of preparing freeze-dried pharmaceutical dosage forms that exhibit rapid dissolution in appropriate solvents.

It is a further additional object of the present invention to provide freeze-dried foams that include active ingredients, such as pharmaceuticals, nutrients, diagnostics, fertilizers and insecticides.

It is a specific object of the present invention to provide a method of preparing freeze-dried foams that include one or more active ingredients. According to the inventive method, a dispersion of a gas and an aqueous solution or suspension is formed that contains the active ingredient dissolved or suspended within the solution or suspension. This dispersion of gas is then maintained while the dispersion is freeze-dried to form a freeze-dried foam that contains the active ingredient dispersed throughout.

In order to maintain the dispersion of the gas within the solution or suspension, it is preferable to include one or more surfactants within the solution or suspension. In addition, it is preferable to include a bulk-forming agent within the suspension or solution such that both the gas and the active ingredient are maintained in a dispersed state within the solution or suspension. Any suitable conventional method of freeze-drying may be employed.

The resulting freeze-dried foams prevent or reduce the incidence of cracking during the freeze-drying process. This is because the stresses that normally build up during the freezing process are harmlessly released due to the porosity of the foam. In addition, the presence of the dispersed gas with the solution or suspension results in a more rapid freeze-drying process, since during both the freezing and the drying steps, vapors are more readily able to penetrate into the interior of the preparation being freeze-dried. Because of this more rapid rate of freeze-drying, the chance of meltback during the freeze-drying process is greatly reduced or eliminated.

In the realm of pharmaceutical use, freeze-dried pharmaceutical dosage forms prepared according to the present invention exhibit rapid dissolution upon contact with physiological solvents, such as water, saliva, or gastrointestinal fluids. Therefore, the present inventive pharmaceutical freeze-dried foams provide a more rapid dispersion of the pharmaceutical within the body upon ingestion.

Further objects and embodiments of the present invention will be made known in the following description of the preferred embodiments and claims. Though the following description of the preferred embodiments focuses on the inclusion of pharmaceuticals as the active ingredient, it is to be understood that the desirable properties of the inventive methods and foams may be advantageously used in connection with many different types of active ingredients including, by way of example, nutrients, vitamins, minerals, diagnostics, fertilizers and insecticides.

DESCRIPTION OF THE PREFERRED EMBODIMENTS

The starting point for preparation of the inventive freeze-dried foams is the solution or suspension to be freeze-dried. This solution or suspension should be primarily aqueous in nature and should contain the desired active ingredient dissolved or suspended therein. Examples of pharmaceutical compositions that can be successfully utilized in connection with the present invention are benzodiazapine, oxazepam, temazepam and lorazepam. However, any pharmaceutical composition that can be freeze-dried conventionally with success may be used in connection with the present invention.

In addition to incorporation of pharmaceutical compositions as the active ingredient, nutritional, diagnostic or other chemical agents may be advantageously incorporated into the inventive freeze-dried foam. Examples of nutritional agents that may be used with the present invention are vitamins, minerals, and food supplements. Diagnostic agents, such as monoclonal antibodies, may be successfully incorporated into the present freeze-dried foams. Other types of active chemical agents may also be used with the present invention, for example, fertilizers and insecticides. Whatever active ingredient is incorporated into the freeze-dried foam, it should be present in the resulting freeze-dried foam in an effective concentration per unit volume.

The selected gas may be incorporated into the solution or suspension by bubbling the gas through the solution or suspension. The gas may be selected from any gas that will not adversely react with the active ingredient. Suitable gases include air, oxygen, nitrogen and argon. It is advantageous to incorporate bubbles of minute, uniform size into the solution or suspension. Preferably, the majority of bubbles range from approximately 50 microns to approximately 500 microns in size. Most preferably, the bubbles are substantially uniform in size and have an average diameter of approximately 100 microns. The advantage of small, uniform bubbles is that it is easier to maintain the gas in a dispersed state within the solution or suspension. To obtain this desirable result, the gas may be first passed through sintered glass immediately before bubbling the gas through the solution or suspension. Alternatively, gas may be incorporated into the solution or suspension by means of high speed mixing.

At least some portion of the gas dispersed within the solution or suspension must be maintained in a dispersed state during the freeze-drying process, since the dispersed gas is necessary to formation of the foam-like structure of the resulting freeze-dried foam. One means for maintaining a sufficient dispersion of the gas within the solution or suspension is to employ a rapid freezing technique. In the use of such techniques, the dispersed gas bubbles are "trapped" within the solution or suspension as it is frozen, thus forming the foam-like structure. Alternatively, one or more surfactant compositions may be incorporated into the solution or suspension. Surfactants aid in maintaining the gas in its dispersed state throughout the suspension or solution during the freezing process. Although any conventional surfactant may be used, preferred surfactant agents include sodium lauryl sulfate, polyoxyethylene sorbitan esters (commercially available under the tradename, Tween), sorbitan esters (commercially available under the tradename, Span) lecithin and sodium dioctylsulphosuccinate. The surfactant compositions, if used, should be present in an amount sufficient to effectively maintain the dispersion of the gas within the solution or suspension.

One or more bulk-forming agents may also be incorporated into the solution or suspension prior to freezing. The bulk-forming agent may be present in addition to a surfactant or to the exclusion of a surfactant. The primary purpose of the bulk-forming agent is to aid in maintaining the dispersion of the active ingredient within the solution or suspension. This is especially helpful in the case of active ingredients that are not aqueously soluble enough such that they must be suspended, rather than dissolved. Additionally, bulk-forming agents aid the maintenance of the dispersion of the gas within the solution or suspension prior to and during the freezing process. Any suitable, conventional bulk-forming agent may be used in connection with the present invention. Preferred bulk-forming agents include long chain polymers, e.g., polypeptides such as gelatin or hydrolyzed gelatin, cellulose derivatives, alginate derivatives, polyvinyl pyrrolidone, polyethylene glycols, polysaccharides, such as dextran, mannitol, sugars and starches, and gums such as acacia, xanthan, and tragacanth. The bulk-forming agents may be incorporated into the solution or suspension in concentrations sufficient to aid in the maintenance of the dispersion of the active ingredient or gas within the solution or suspension.

The resulting solution or suspension having gas dispersed therethrough may be freeze-dried by any conventional freeze-drying process. For example, the solution or suspension may be frozen by dispensing the solution or suspension into preformed molds and subsequently freezing such molds on refrigerated shelves or in refrigerated chambers. Alternatively, the molds containing the solution or suspension may be passed through a stream of cold gas or vapor, such as liquid nitrogen in a freezing tunnel.

As an alternative to the use of molds, the solutions or suspensions having gas dispersed therein may be frozen in dropwise fashion. For example, the solution or suspension may be pumped or fed under gravity through an orifice in order to form drops, spheres or a spray of small particles. These drops can then be frozen by passage through a cold gas or liquid, for example, liquid nitrogen or liquid nitrogen vapor. Another possibility is that drops of the solution or suspension may be frozen in a chilled liquid that is incompatible with the solution or suspension. In such cases, the relative densities of the liquid and the solution or suspension are controlled such that the drops can either pass through the chilled incompatible liquid as it freezes or, alternatively, the frozen droplet may float on the surface of the chilled incompatible liquid. This latter flotation feature facilitates the collection of the frozen droplets. An example of a liquid that may be chilled and that is incompatible with most primarily aqueous solutions or suspensions is trichloroethylene.

The use of dropwise forms of freezing is particularly advantageous in the preparation of the inventive freeze-dried foams since it allows for the rapid freezing of the solution or suspension. This in turn limits the amount of gas that can escape from its dispersed state within the solution or suspension. In addition, the presence of the gas in the solution or suspension being frozen decreases the freezing time and virtually eliminates cracking because of the porosity of the solution or suspension.

The frozen solution or suspension is then dried on heated shelves in a partially or completely evacuated chamber in accordance with conventional freeze-drying methods. In the case of frozen molded forms of the solution or suspension, these forms may be forced through an extrusion device such that the frozen solution or suspension is cut or formed into appropriately sized segments prior to drying. The drying process is relatively rapid due to the porous nature of the frozen droplets or molded forms. Furthermore, because the drying process is relatively rapid, the phenomenon of meltback is completely avoided or substantially reduced. The resulting freeze-dried product has a foam-like structure and includes the active ingredient dispersed therethrough. In the case of pharmaceutical freeze-dried dosage forms, the resulting dosage forms exhibit extremely rapid dissolution when placed in water or in the human mouth. Such rapid dissolution is desirable in order to introduce the pharmaceutical into the physiological system as soon as possible.

Of course, secondary components such as flavorings, preservatives or colorings may also be incorporated in the freeze-dried foams in accordance with conventional practices.

COMPARATIVE EXAMPLES 1-6

In Examples 1-6, the BOC freezing machine described in United Kingdom Pat. No. 2117222A was used to accomplish freezing of the solutions or suspensions. In each example, a solution containing 4% by weight of gelatin and 3% by weight of mannitol in water was dispersed dropwise into the liquid nitrogen flowing down the V-shaped channel of the BOC freezing machine. The solutions frozen in Examples 4-6 also contained 6.67% by weight of oxazepam as the active pharmaceutical ingredient. The drops rolling along this channel froze from the outside to the center. A typical residence time for the drops in the freezing channel was about 8-10 seconds. During this time, the surface of the drops froze, but not the core of the drops. Complete freezing occured after the sphere had been separated from the liquid nitrogen in the freezing machine and was left exposed to the cold nitrogen exhaust gas. The resulting frozen drops were then freeze-dried on heated shelves in an evacuated chamber. The mean diameters, dosage weights, disintegration times, cracking rates, and drying times for Examples 1-6 are shown below in Table I.

TABLE I

| Example | Mean Diameter (mm.) | Dosage Weight (g.) | Disintegration time at 37° C. | % Cracking | Drying time (mins.) |
|---|---|---|---|---|---|
| 1 | 5.5 | 0.1 | 4.5 sec. | 100 | 233 |
| 2 | 6.9 | 0.175 | 5.6 sec. | 100 | 260 |
| 3 | 7.9 | 0.25 | 6.5 sec. | 100 | 260 |
| 4 | 5.8 | 0.1 | 4.5 sec. | 100 | 293 |
| 5 | 7.2 | 0.175 | 6.3 sec. | 100 | 300 |
| 6 | 8.1 | 0.25 | 7.0 sec. | 100 | 300 |

The disintegration times noted are the times taken to wet the freeze-dried droplet dosage form. In all cases, the dispersion of the disintegrated dosage form in water was poor.

COMPARATIVE EXAMPLES 7 AND 8

In Examples 7 and 8, placebo freeze-dried dosage forms made from solutions without incorporated gas were dispersed dropwise into a flask containing liquid nitrogen. The resulting drops floated on the surface of liquid nitrogen initially. However, the droplets sank immediately once the temperature of the drop had reached the approximate temperature of liquid nitrogen, i.e., −196° C. The frozen droplets were collected by decanting the liquid nitrogen. The frozen droplets were freeze-dried on heated shelves in an evacuated chamber. In Example 7, the placebo dosage form included 4% hydrolyzed gelatin and 3% mannitol by weight in water. Example 8 contained 4% gelatin and 3% mannitol by weight in water. The mean diameters, dosage weights, disintegration times, cracking rates and drying times for Examples 7 and 8 are shown below in Table II.

TABLE II

| Example | Mean Diameter (mm.) | Dosage Weight (g.) | Disintegration time at 37° C. | % Cracking | Drying time (mins.) |
|---|---|---|---|---|---|
| 7 | 5.0 | 0.07 | Instantaneous | 100 | Dried overnight |
| 8 | 4.5 | 0.07 | Instantaneous | 100 | 150 |

EXAMPLES 9-18

Examples 9-18 represent freeze-dried foam dosage forms prepared in accordance with the present invention. In each case, solutions containing 4% by weight gelatin and 3% mannitol in water were prepared. Additional components were added as noted in Table III. Air bubbles were incorporated into the solutions and suspensions by use of a Silverson homogenizer. All of the air bubbles incorporated into the solution and suspension were of relatively uniform size and had an average diameter of approximately 100 microns. The resulting solutions and suspensions were dispensed dropwise into a flask containing liquid nitrogen. The spheres floated not only during freezing, but also continued to float once completely frozen. This facilitated the removal of the frozen droplets from the liquid nitrogen. The mean diameters, dosage weights, disintegration times, cracking rates and drying times for Examples 9-18 are shown below in Table III. Dispersion of each of the dosage forms in Examples 9-18 was excellent upon disintegration in water.

TABLE III

| Example | Additional Components | Mean Diameter (mm.) | Dosage Weight (g.) | Disintegration time at 37° C. | % Cracking | Drying time (min.) |
|---|---|---|---|---|---|---|
| 9 | 3% Tween 80 | 6.5 | 0.09-0.10 | 0.5 sec. | 0 | 150 |
| 10 | 1% sodium dioctyl sulphosuccinate | 6.5 | 0.09-0.10 | 0.3 sec. | 0 | 180 |
| 11 | 1% sodium dioctyl sulphosuccinate 6.67% Oxazepam | 6.3 | 0.09-0.10 | Instantaneous | 0 | 110 |
| 12 | 0.25% sodium dioctyl sulphosuccinate | 6.5 | 0.09-0.10 | Instantaneous | 0.8 | 121 |
| 13 | 1% sodium lauryl sulphate | 6.51 | 0.09-0.10 | Instantaneous | 0 | 155 |
| 14 | 0.25% sodium lauryl sulphate | 7.5 | 0.09-0.10 | Instantaneous | 6 | 120 |
| 15 | 6.67% Oxazepam 0.25% sodium lauryl sulphate | 7.5 | 0.09-0.10 | Instantaneous | 4 | 135 |
| 16 | 0.67% Lorazepam 0.25% sodium lauryl sulphate | 7.3 | 0.09-0.10 | Instantaneous | 16.8 | 137 |
| 17 | 6.67% Oxazepam | 7.7 | 0.09-0.10 | Instantaneous | 0 | 135 |
| 18 | 0.67% Lorazepam | 8.0 | 0.09-0.10 | Instantaneous | 0.4 | — |

As can be seen by a comparison of Tables I and II to the inventive compositions shown in Table III, the freeze-dried dosage forms produced according to the present invention are superior to the dosage forms prepared according to the prior art in several respects. First, the drying time for the inventive formulations is in most cases significantly shorter. This is believed to be due to the increased porosity of the foamed solutions or suspensions. Second, the inventive formulations exhibit far less cracking than the freeze-dried formulations prepared according to prior art. This is believed due to the ability of the foamed solutions or suspensions to harmlessly release the tensions that build up during the freezing process. Third, the disintegration rates of the inventive formulations are noticably shorter in some cases than the droplet formulations prepared according to the prior art. In the area of pharmaceutical formulations, rapid disintegration time is desirable since it can often enhance the onset of the pharmacological properties of the drug being administered.

It is to be understood that the preceeding description of the preferred embodiments has emphasized certain embodiments by way of example. Numerous other embodiments not specifically discussed may fall within the spirit and scope of the present invention and the following claims.

I hereby claim as my invention:

1. A method of preparing an effective unit dosage form of an active ingredient, said active ingredient being selected from the group consisting of pharmaceuticals, nutrients, vitamins, minerals, diagnostic agents, fertilizers and insecticides, comprising the following steps in combination:
    a. forming a dispersion of a gas and a solution or suspension, said solution or suspension containing said active ingredient dissolved or suspended therein;
    b. maintaining said gas in a dispersed state within said dispersion; and
    c. freeze-drying a unit volume of said dispersion to form a freeze-dried foam containing said active ingredient dispersed therethrough, said freeze-dried unit volume containing an effective unit dosage of said active ingredient.

2. The method of claim 1 wherein said dispersion additionally comprises a surfactant that aids in maintaining said gas in a dispersed state.

3. The method according to claim 2 wherein said surfactant is sodium lauryl sulfate, sodium dioctyl sulphosuccinate, a polyoxyethylene sorbitan ester, a sorbitan ester, or lecithin.

4. The method according to claim 1 wherein said dispersion additionally comprises a bulk-forming agent that aids in maintaining said active ingredient in a dispersed state within said solution or suspension.

5. The method according to claim 4 wherein said bulk-forming agent is a polypeptide, a cellulose derivative, an alginate derivative, a polyvinyl pyrrolidone, a polyethylene glycol, a polysaccharide, or a gum.

6. The method according to claim 5 wherein said bulk-forming agent is a polypeptide selected from the group consisting of gelatin and hydrolyzed gelatin.

7. The method according to claim 5 wherein said bulk-forming agent is a polysaccharide selected from the group consisting of dextran, mannitol, sugars and starches.

8. The method according to claim 5 wherein said bulk-forming agent is a gum selected from the group consisting of acacia, xanthan and tragacanth.

9. The method according to claim 1 wherein said gas is dispersed within said solution or suspension by means of high speed mixing.

10. The method according to claim 1 wherein said gas is dispersed within said solution or suspension by bubbling said gas through said solution or suspension.

11. The method according to claim 10 wherein said gas is dispersed within said solution or suspension in the form of bubbles of relatively uniform size.

12. The method of claim 11 wherein said bubbles range in size from approximately 50 microns to approximately 500 microns.

13. The method according to claim 1 wherein said gas is air, oxygen, nitrogen or argon.

14. The method according to claim 1 wherein said dispersion additionally contains a flavoring, preservative or coloring agent.

15. The method of claim 1 wherein said unit volume of said dispersion comprises a drop of said solution or suspension.

16. A method of preparing an effective unit dosage form of a pharmaceutical composition, comprising the following steps in combination:
    a. forming a dispersion of a gas and a solution or suspension, said solution or suspension containing said pharmaceutical composition dissolved or suspended therein;
    b. maintaining said gas in a dispersed state within said dispersion; and
    c. freeze-drying a unit volume of said dispersion to form a freeze-dried foam containing said pharmaceutical composition dispersed therethrough, said freeze-dried unit volume containing an effective unit dosage of said pharmaceutical composition.

17. The method of claim 16 wherein said unit volume of said dispersion comprises a drop of said solution or suspension.

18. An effective unit dosage form of an active ingredient prepared according to a method comprising the following steps in combination:
    a. forming a dipsersion of a gas and a solution or suspension, said solution or suspension containing said active ingredient dissolved or suspended therein;
    b. maintaining said gas in a dispersed state within said dispersion; and
    c. freeze-drying a unit volume of said dispersion to form a freeze-dried foam containing said active ingredient dispersed therethrough, said freeze-dried unit volume containing an effective unit dosage of said active ingredient;
said active ingredient being selected from the group consisting of pharmaceuticals, nutrients, vitamins, minerals, diagnostic agents, fertilizers and insecticides.

19. The effective unit dosage form of claim 18 wherein said active ingredient is a pharmaceutical.

* * * * *